United States Patent [19]

Cook et al.

[11] 4,272,455

[45] Jun. 9, 1981

[54] PRODUCTION OF MONOALKYLENEGLYCOLS, MONOALKANOLAMINES AND ALKYLENEDIAMINE

[75] Inventors: Frank T. Cook; Daniel W. Baugh, Jr.; Robert V. Chambers, Jr., all of Baton Rouge, La.

[73] Assignee: The Dow Chemical Company, Midland, Mich.

[21] Appl. No.: 107,287

[22] Filed: Dec. 26, 1979

[51] Int. Cl.$^3$ .................... C07C 29/00; C07C 85/145; C07C 85/20; C07C 89/00

[52] U.S. Cl. .................................. 564/503; 548/347; 560/157; 568/852; 568/858; 568/867; 564/511; 548/229; 548/317

[58] Field of Search .................. 260/583 P, 584 R; 568/852

[56] References Cited

U.S. PATENT DOCUMENTS

| | | | |
|---|---|---|---|
| 2,448,767 | 9/1948 | Carlson | 260/584 R X |
| 2,812,333 | 11/1957 | Steele | 260/584 R X |
| 2,826,587 | 3/1958 | Trask et al. | 260/307 |
| 2,847,418 | 8/1958 | Steele | 260/309.7 |
| 2,892,843 | 6/1959 | Levine | 260/309.7 |
| 2,975,187 | 3/1961 | Lynn | 260/307 |
| 3,133,932 | 5/1964 | Horn et al. | 260/307 |
| 3,149,154 | 9/1964 | Cluff et al. | 260/534 |
| 3,152,180 | 10/1964 | Haaf | 260/561 |
| 3,190,882 | 6/1965 | Schaeffer | 260/268 |
| 3,232,936 | 2/1966 | Reynolds | 260/584 R X |
| 3,592,854 | 7/1971 | Potts et al. | 260/583 |

FOREIGN PATENT DOCUMENTS

| | | | |
|---|---|---|---|
| 600253 | 6/1960 | Canada | 260/584 R |
| 442413 | 3/1925 | Fed. Rep. of Germany | 260/583 P |
| 446547 | 7/1925 | Fed. Rep. of Germany | 260/583 P |
| 2263715 | 7/1973 | Fed. Rep. of Germany | 260/584 R |
| 37-80 | 1/1962 | Japan | 260/583 P |
| 45-21291 | 7/1970 | Japan | 260/584 R |

OTHER PUBLICATIONS

Viard, "Chem. Ab.", vol. 53, Ab. No. 6253$^f$ (1959).
Heathenck et al., "Chem. Ab.", vol. 59, Ab. No. 3903$^h$ (1963).
Helmuth et al., "Chem. Ab.", vol. 49, Ab. No. 3943$^d$ (1955).
Dyen et al., "Chem. Rev.", vol. 67, pp. 197–221 (1967).
McKay et al., "J. Org. Chem.", vol. 16, pp. 1829–1834, (1951).
Beachell et al., "J. Polym. Sc.", Parta, vol. 2, pp. 4773–4785 (1964).
Desseigne, "Chem. Ab.", vol. 58, Ab. No. 6691$^c$ (1963).
Ehret, "College Chem.", (Smith's), 6th Ed., p. 501 (1946).
Teramura et al., "Chem. Ab.", vol. 55, Ab. No. 5523 (1961).
Fumasoni et al., "Annali di Chimica", 63, pp. 873–882 (1973).
Dyer et al., "JACS", 79, pp. 672–675 (1957).
Ibbotson, "Chem. Ab.", 81, Ab. No. 78662j (1974).

*Primary Examiner*—John Doll
*Attorney, Agent, or Firm*—A. J. Young

[57] ABSTRACT

A method for the formation of monoalkyleneglycols, monoalkanolamines and alkylenediamines, comprising the steps of: (a) reacting ammonia or ammonium carbonate with an alkylenecarbonate to form a carbamate, (b) heating the carbamate to form a monoalkyleneglycol, an alkyleneurea and a 2-oxazolidinone, (c) further reacting the alkyleneurea and the 2-oxazolidinone with ammonium hydroxide to form ammonia or ammonium carbonate, a monoalkanolamine, and an alkylenediamine, (d) separating the ammonia or ammonium carbonate, the monoalkyleneglycol, the alkylenediamine, and the monoalkanolamine, and (e) recycling the ammonia or ammonium carbonate to reaction step (a).

10 Claims, No Drawings

PRODUCTION OF MONOALKYLENEGLYCOLS, MONOALKANOLAMINES AND ALKYLENEDIAMINE

BACKGROUND OF THE INVENTION

This invention relates to the production of glycols and amines. More particularly, the invention relates to a cyclic process for preparing monoalkyleneglycols, monoalkanolamines and alkylenediamines from ammonia or ammonium carbonate and an alkylene carbonate.

The production of monoalkyleneglycols is usually carried out by reacting water with an olefin oxide:

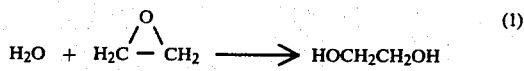 (1)

This method suffers from the disadvantage that dialkyleneglycols and trialkyleneglycols are made as by-products:

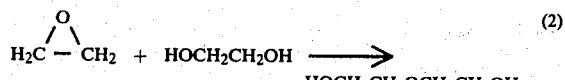 (2)

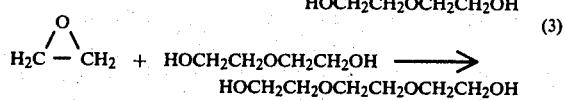 (3)

The production of monoalkanolamines is usually carried out by reacting ammonia with an olefin oxide:

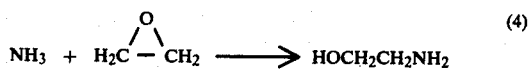 (4)

This method suffers from the disadvantage that dialkanolamines and trialkanolamines are made as by-products:

 (5)

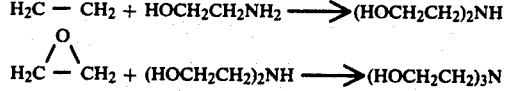 (6)

Alkylenediamines are usually prepared by the reaction of ammonia or ammonium hydroxide with alkylene dichlorides:

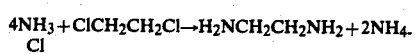 (7)

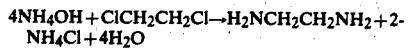 (8)

This method suffers the disadvantage of making ammonium chloride ($NH_4Cl$) as a by-product.

It is an object of this invention to provide a method of producing monoalkyleneglycols substantially free of dialkyleneglycols and trialkyleneglycols, monoalkanolamines substantially free of dialkanolamines and trialkanolamines, and alkylenediamines without ammonium chloride. It is a further object of the invention to provide an efficient, cyclic process for the production of monoalkyleneglycols, monoalkanolamines and alkylenediamines. Other objects of the invention will be apparent to those skilled in the art in the specification and examples which hereinafter follow.

SUMMARY

The present invention provides a method for the preparation of monoalkyleneglycols, monoalkanolamines and alkylenediamines. The invention has the advantages of producing monoalkyleneglycols substantially free of dialkyleneglycol and trialkyleneglycol by-products, of producing monoalkanolamines substantially free of dialkanolamine and trialkanolamine by-products, of producing alkylenediamines without the formation of ammonium chloride as a by-product, and of regenerating one of the reactants in the final reaction step, thereby permitting a cyclic process.

In general, the method of this invention comprises the following steps or their equivalents: (a) reacting an alkylene carbonate with ammonia or ammonium carbonate to form a carbamate; (b) heating the carbamate to form a monoalkyleneglycol, an alkyleneurea, a 2-oxazolidinone or a mixture thereof; (c) further reacting the alkyleneurea, the 2-oxazolidinone, or a mixture thereof with ammonium hydroxide to form an alkylenediamine, a monoalkanolamine or a mixture thereof, and to form ammonia or ammonium carbonate; (d) separating the monoalkyleneglycol, alkylenediamine, monoalkanolamine, and the ammonia or ammonium carbonate; and (e) recycling the ammonia or ammonium carbonate to the first reaction step (a).

The method is further illustrated by the following reactions:

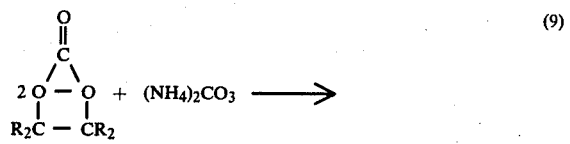 (9)

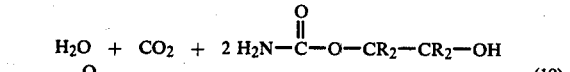 (10)

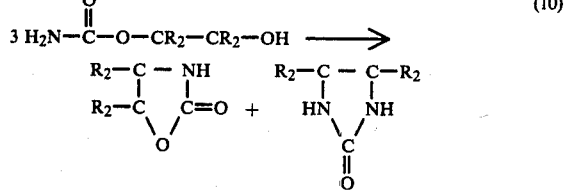 (11)

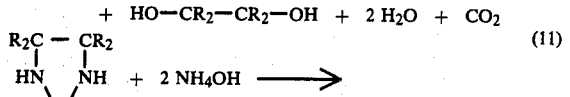 (12)

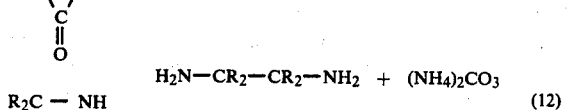

In the above equations R represents hydrogen, an alkyl group or an aryl group.

DESCRIPTION OF THE PREFERRED EMBODIMENTS

The following description illustrates the manner in which the principles of the invention are applied, but is not to be construed as limiting the scope of the invention.

More specifically, the present invention comprises the following preferred steps or their equivalents:

(a) reacting ammonia or ammonium carbonate with ethylene carbonate to form beta-hydroxyethyl carbamate, (b) heating the beta-hydroxyethyl carbamate to between about 180° C. and about 350° C. to form monoethyleneglycol, ethyleneurea, 2-oxazolidinone, or a mixture thereof, (c) further reacting the ethyleneurea, the 2-oxazolidinone, or a mixture thereof with ammonium hydroxide to form ethylenediamine, monoethanolamine, or a mixture thereof, and to form ammonia or ammonium carbonate, (d) separating the monoethyleneglycol, ethylenediamine, monoethanolamine, and the ammonia or ammonium carbonate, and (e) recycling the ammonia or ammonium carbonate to the first reaction step (a).

The temperature of reaction step (b) may preferably be controlled between about 210° C. and about 300° C., and more preferably between about 210° C. and about 220° C. to maximize the yield of 2-oxazolidinone or between about 275° C. and about 285° C. to maximize the yield of ethyleneurea. Preferably, the molar ratio of ammonia or ammonium carbonate is between about one to about two moles per mole of ethylene carbonate in reaction step (a), the molar ratio of ammonium hydroxide is between about two to about four moles per mole of ethyleneurea and of 2-oxazolidinone in reaction step (c), the temperature for reaction step (a) is preferably between about 20° C. and about 100° C. and more preferably between about 50° C. and about 60° C., and the temperature for reaction step (c) is preferably between about 50° C. and about 200° C.

EXAMPLE 1

This example illustrates the preparation of beta-hydroxyethyl carbamate from ethylenecarbonate. Four hundred twenty grams of ethylene carbonate (4.77 moles) was placed in a round-bottom flask equipped with a heating mantle. The contents of the flask were mixed throughout the experiment by means of a magnetized stirring bar. The ethylene carbonate was warmed to 57° C. Thereafter, six hundred fifty-three grams (6.81 moles) of crushed ammonium carbonate was added to the flask and admixed with the ethylene carbonate. The reaction mixture was held at 57° C. until all of the ammonium carbonate had decomposed. The resulting solution was then stripped of ammonia at 100° C. under a pressure of ten millimeters of mercury. Four hundred ninety-three and one-half grams of the reaction product were recovered. The product was analyzed by nuclear magnetic resonance, which indicated the substantial absence of ethylenecarbonate and by-products. The yield of beta-hydroxyethyl carbamate was 98.5% of theoretical.

EXAMPLE 2

This example illustrates the thermal decomposition of betahydroxyethyl carbamate to monoethyleneglycol, ethyleneurea and 2-oxazolidinone at 240° C. and 220° C. The reactor comprised a preheated coil in series with a one-inch pipe. The pipe was packed with glass helices, and the beta-hydroxyethyl carbamate was pumped through the packed pipe, which was maintained at 240° C. in one experiment and at 220° C. in a second experiment, at a rate to provide a residence time in the pipe of about thirty minutes. The resulting products were a mixture of 23% 2-oxazolidinone, 7% ethyleneurea, and 70% monoethyleneglycol by weight for the experiment performed at 240° C., and of 24% 2-oxazolidinone and 75% monoethyleneglycol for the experiment at 220° C., all percentages being expressed on a weight basis.

EXAMPLE 3

This example illustrates the thermal decomposition of betahydroxyethyl carbamate to ethyleneurea and 2-oxazolidinone at 280° C. The reactor and residence time were the same as in Example 2, but the reaction temperature was 280° C. Under these conditions the product distribution was 12% 2-oxazolidinone, 20% ethyleneurea, and 68% monoethyleneglycol (weight basis).

EXAMPLE 4

This example illustrates the hydrolysis of ethyleneurea to ethylenediamine. A one-liter Parr reactor was charged with twenty-four grams of ethyleneurea and two hundred and fifty milliliters of about 18 normal concentrated ammonium hydroxide. The reactor was sealed and heated, with stirring, to 200° C. and maintained at this temperature for three hours. The reactor was then allowed to cool, and the product mixture was analyzed by gas chromatography. The analytical results and calculations indicated 60% conversion of the ethyleneurea, with a 90% selectivity to ethylenediamine.

EXAMPLE 5

This example illustrates the hydrolysis of 2-oxazolidinone to monoethanolamine. A one-liter Parr reactor was charged with two hundred and twenty grams of 2-oxazolidinone and two hundred and fifty milliliters of about 18 normal concentrated ammonium hydroxide. The reactor was sealed and heated, with stirring, to 150° C. This temperature was maintained for one hour. The reactor was then allowed to cool, and the product mixture was analyzed by gas chromatography. The analytical results and calculations indicated 84% conversion of the 2-oxazolidinone, with a 93% selectivity to monoethanolamine.

While certain representative embodiments and details have been shown for the purpose of illustrating the invention, it will be apparent to those skilled in the art that various changes and modifications can be made therein without departing from the spirit and scope of the invention.

What is claimed is:

1. A process for the production of monoalkyleneglycols, monoalkanolamines and alkylenediamines, comprising the steps of:
   a. reacting an alkylene carbonate with ammonia or ammonium carbonate to form a carbamate;
   b. heating the carbamate to form a monoalkyleneglycol, an alkyleneurea, a 2-oxazolidinone, or a mixture thereof;
   c. further reacting the alkyleneurea, the 2-oxazolidinone, or a mixture thereof with ammonium hydroxide to form an alkylenediamine, a monoalkanolamine, or a mixture thereof, and to form ammonia or ammonium carbonate; and d. separating the monoalkyleneglycol, the alkylenediamine, the monoalkanolamine, and the ammonia or ammonium carbonate.

2. The process of claim 1 wherein the alkylene carbonate is reacted with ammonia.

3. The process of claim 1 wherein the alkylene carbonate is reacted with ammonium carbonate.

4. The process of claim 1, further comprising the step of:

e. recycling the ammonia or ammonium carbonate to reaction step (a).

5. The process of claim 4 wherein the molar ratio of ammonia or ammonium carbonate is between about one and about two moles per mole of alkylene carbonate and the molar ratio of ammonium hydroxide is between about two and about four moles per mole of alkyleneurea and of 2-oxazolidinone.

6. The process of claim 5 wherein the alkylene carbonate is ethylene carbonate.

7. The process of claim 6 wherein the temperature for reaction step (a) is between about 20° C. and about 100° C., the carbamate is heated to between about 180° C. and about 350° C. in reaction step (b), and the temperature for reaction step (c) is between about 50° C. and about 200° C.

8. The process of claim 7 wherein the temperature for reaction step (a) is between about 50° and about 60° C. and the carbamate is heated to between about 210° C. and about 300° C. in reaction step (b).

9. The process of claim 8 wherein the carbamate is heated to between about 210° C. and about 220° C.

10. The process of claim 8 wherein the carbamate is heated to between about 275° C. and about 285° C.

* * * * *